United States Patent [19]
Beard

[11] Patent Number: 4,937,880
[45] Date of Patent: Jul. 3, 1990

[54] FACE SHIELD

[76] Inventor: Jeffrey C. Beard, 24 Stoney Creek, Austin, Tex. 78734

[21] Appl. No.: 357,357

[22] Filed: May 26, 1989

[51] Int. Cl.⁵ .............................................. A61F 9/00
[52] U.S. Cl. ..................................... 2/9; 2/8; 2/13; 2/427; 2/429; 128/206.21; 128/857
[58] Field of Search ................ 2/6, 9, 13, 12, 421, 2/2, 426, 427, 428, 429, 430, 8; 128/206.21, 857, 863

[56] References Cited

U.S. PATENT DOCUMENTS

| | | | |
|---|---|---|---|
| 2,086,208 | 7/1937 | Brekelbaum | 2/8 |
| 2,154,774 | 4/1939 | Rienacker et al. | 2/8 |
| 2,249,239 | 7/1941 | Goldsmith | 2/8 |
| 2,363,461 | 11/1944 | Huntsman | 2/8 |
| 2,384,765 | 9/1945 | O'Reilly | 2/8 |
| 2,388,713 | 11/1945 | Schutz et al. | 2/9 |
| 2,419,649 | 4/1947 | Lieg | 2/8 |
| 2,569,715 | 10/1951 | Green | 2/8 |
| 2,668,951 | 2/1954 | MacLean | 2/8 |
| 3,103,667 | 9/1963 | Rogowski | 2/9 |
| 3,152,588 | 10/1964 | Rogowski | 2/9 X |
| 3,298,031 | 1/1967 | Morgan | 2/427 |
| 3,517,392 | 6/1970 | Hodge et al. | 2/8 |
| 3,671,976 | 6/1972 | Johnson et al. | 2/430 |
| 3,868,726 | 3/1975 | LaMarre et al. | 2/8 |
| 4,185,328 | 1/1980 | Graveno | 2/8 |
| 4,250,577 | 2/1981 | Smith | 2/427 |
| 4,288,878 | 9/1981 | Helmbreck | 2/431 X |
| 4,449,255 | 5/1984 | Dodd | 2/428 |
| 4,527,292 | 6/1985 | Kasama et al. | 2/426 X |
| 4,653,124 | 3/1987 | McNeal et al. | 2/427 |
| 4,764,990 | 8/1988 | Markert | 2/429 |

FOREIGN PATENT DOCUMENTS 871946  2/1953  Fed. Rep. of Germany .............. 2/9

Primary Examiner—Werner H. Schroeder
Assistant Examiner—Jeanette E. Chapman
Attorney, Agent, or Firm—John S. Schneider

[57]  ABSTRACT

A shield to protect a wearer's face from liquids, light solids, and objects in the air includes a face mask that is configured in the abstract shape of a face. The mask has an opening in the eye area that accommodates the eye piece parts of goggles. The mask also has a nose piece and lateral extensions that protrude from at least each side of the face mask. Attachment means are provided including means on the face mask and means on the goggles that releasably attach the goggles to the face mask.

6 Claims, 2 Drawing Sheets

FIG. 3
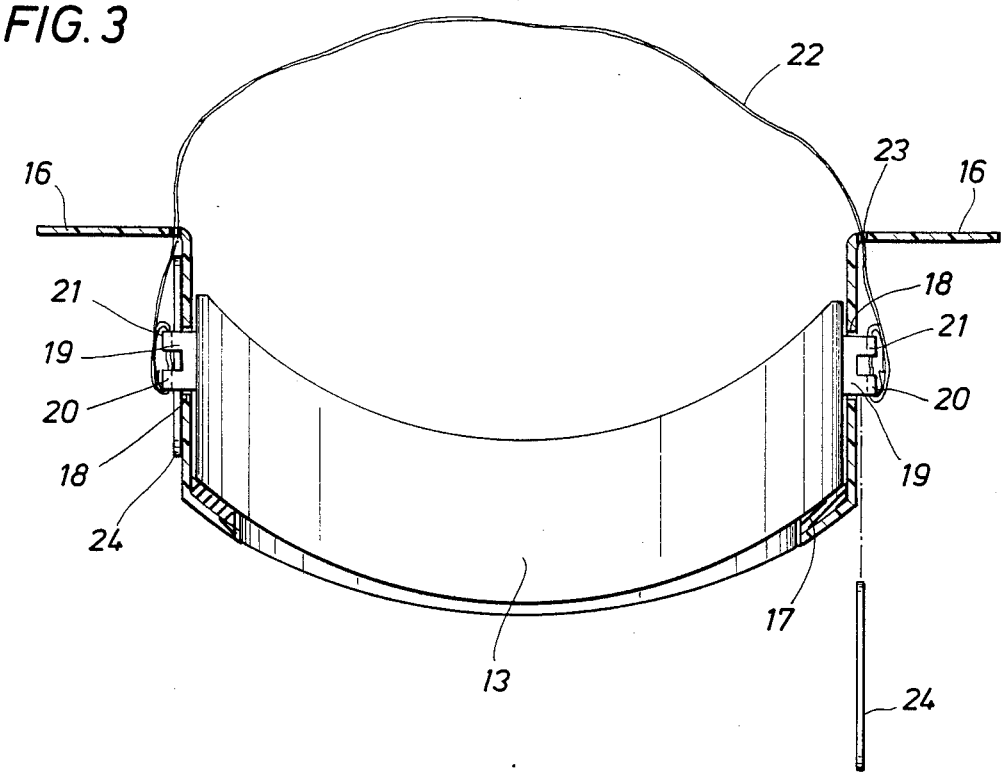
FIG. 4
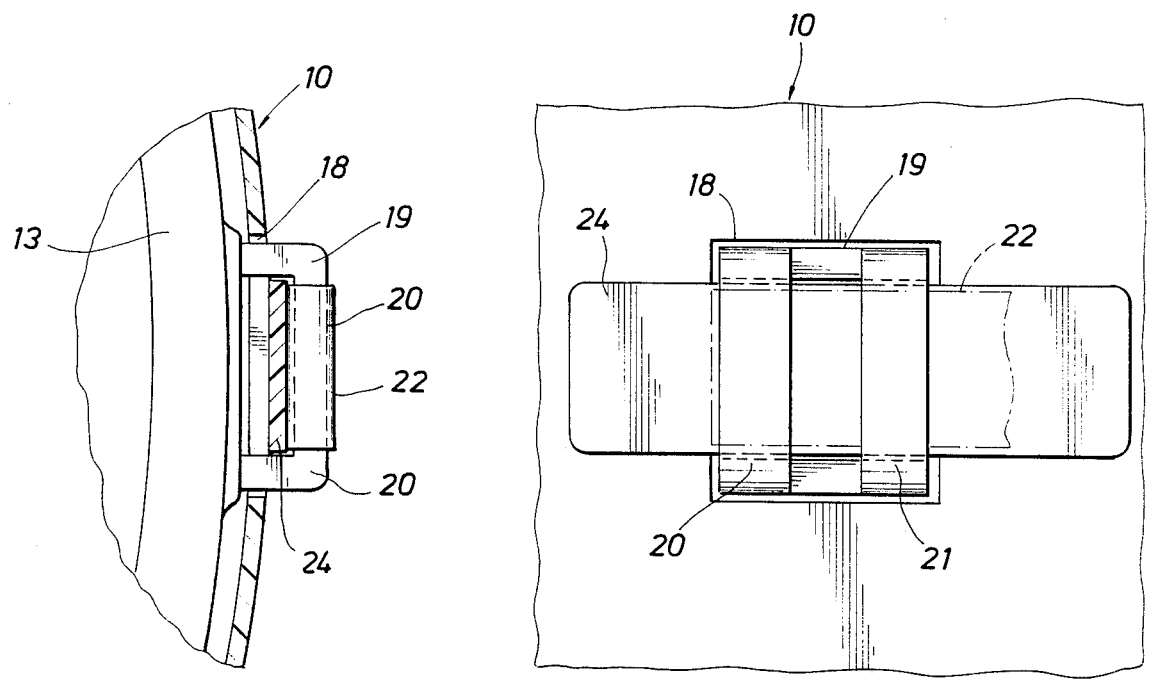
FIG. 5

FACE SHIELD

FIELD OF THE INVENTION

This invention concerns a shield designed to protect the face from liquids, light solids, particles and objects in the air. More particularly, the invention concerns an impact resistant and splash resistant face mask that fits over and attaches to goggles to provide improved vision and breathing.

DESCRIPTION OF THE PRIOR ART

Protective face masks of various designs, shapes and sizes are known; however, none combines the unique features of the present invention. None provides a face mask that protects the wearer's forehead, ears, nose, mouth, chin and sides of the face, and that is releasably attachable to goggles that protect the eyes.

SUMMARY OF THE INVENTION

Briefly, the invention comprises a face shield that includes a face mask that fits over and is releasably attachable to goggles to protect the entire face from liquid, light solids, particles and objects in the air. The face mask, preferably molded of polymeric material, is formed in the abstract shape of a face having curved portions covering the forehead, sides of the face and with an opening in the eye area of the face. The face mask includes a nosepiece covering the nose, mouth and chin with a curved portion covering under-the-chin and extensions that protrude laterally from at least two sides thereof. Attachment means are provided including means on the face mask that cooperate with means on the goggles to releasably attach the goggles to the face mask. Seal means on the face mask surrounds the opening in the eye area and is engageable with areas surrounding eye pieces on the goggles to seal off contacting eye areas of the face mask and the goggles.

BRIEF DESCRIPTION OF THE DRAWINGS

FIG. 3 is a view taken along lines 3—3 of FIG. 1;

FIG. 4 is an enlarged front elevational view of the face mask-goggles attachment devices; and FIG. 5 is an enlarged side view of the face mask-goggles attachment devices shown in FIG. 4.

DESCRIPTION OF THE PREFERRED EMBODIMENTS

Figure 2:
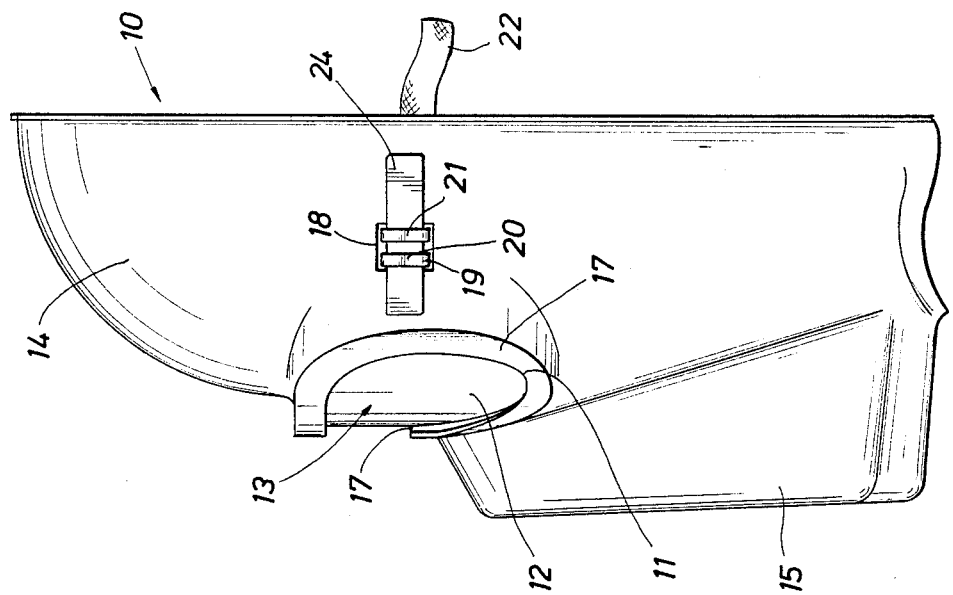
FIG. 2 is a view taken on lines 2—2 of FIG. 1.
Figure 1:
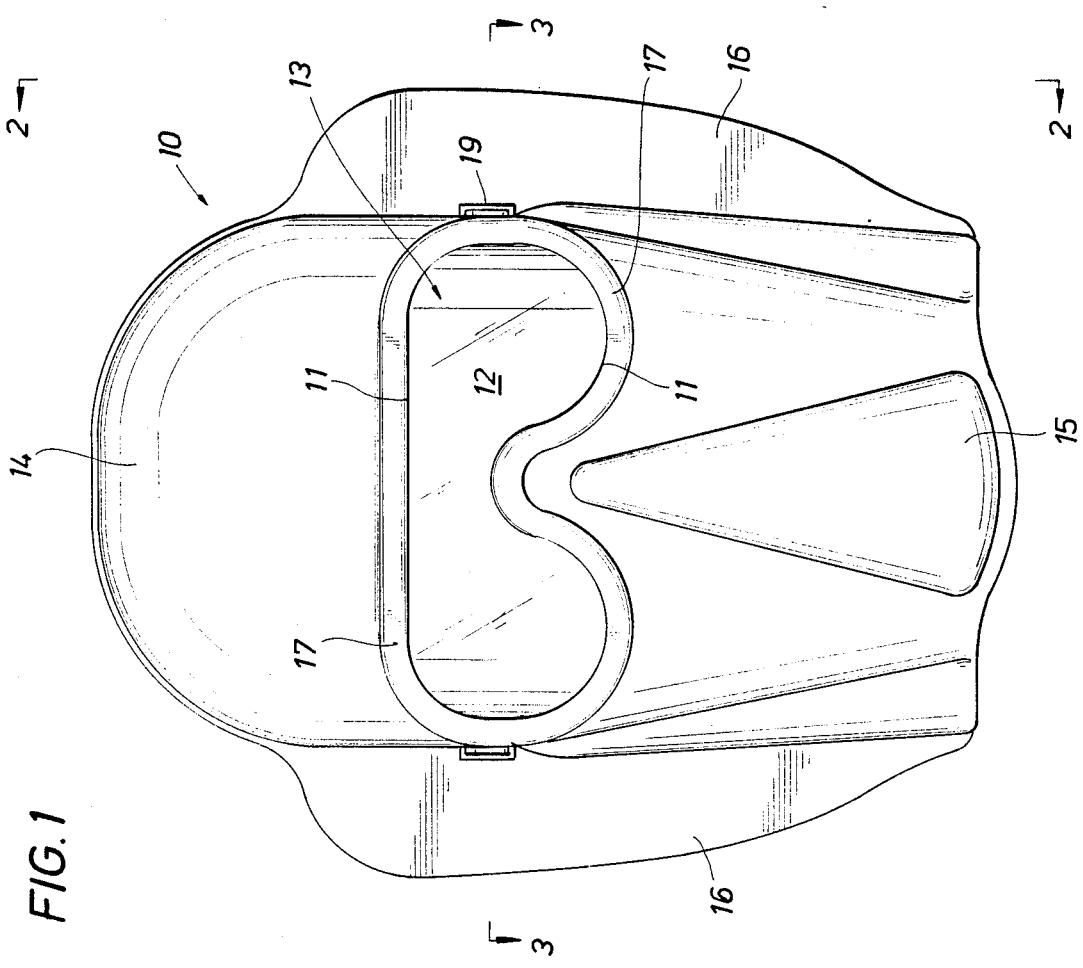
FIG. 1 is a front elevational view of the face mask of the invention with goggles in position in the face mask.

Referring to FIGS. 1 and 2 there is shown a face mask, generally desiqnated 10, that has an opening eye area outlined at 11 to accommodate the eye pieces 12 of goggles, generally indicated at 13 (See FIG. 3), a curved forehead portion 14, a nosepiece 15 covering the nose, mouth, chin and including a curved under-the-chin portion extensions 16 protruding from each side of mask 10, a seal inside mask 10, indicated at 17 in FIGS. 1 and 2 and shown in FIG. 3, formed of rubber or the like, surrounds the eye area opening 11 and openings 18 formed in each side of mask 10. Also, shown in FIGS. 1 and 2 are lugs 19 that are attached to the exterior sides of goggles 13. Each lug 19 has parallel spaced apart projecting parts 20 and 21.

Referring particularly to FIGS. 3, 4 and 5 a headstrap 22 having two ends extends through slit openings 23 formed in extension members 16 on each side of face mask 10 one end of strap 22 is threaded over projections 20 and 21 on one side of face mask 10, looped back under both of such projections and then looped over the projections, as shown, thereby tying that end of strap 22 to lug 19 on that one side of ace mask 10. The other end of strap 22 is similarly tied to lug 19 on the other side of face mask 10. Alternatively, one end of strap 22 may be threaded over projections 20 and 21, looped back"; same line, cancel "Each end of strap 22 is threaded under both projections 20 and 21 and then looped back over projection 21 and under projection 20 to tie the one end of one lug strap 22 to 19. Then rectangular locking piece 24 slide under strap 22 on each side of face mask to secure each end of strap 22 to a lug, 19. Seal 17, as seen in FIG. 3 seals against the eye pieces of goggles 13.

Face mask 10 is preferably formed of a tough, impact resistant and splash resistant polymeric material such as polyethylene. The space in the interior of face mask 10 allows breathing space between the individual's face and mask 10. The nose portion 15 provides ample space for breathing apparatus under face mask 10, if desired.

Although polymeric materials are preferred, other materials including glass and metals may be used for the material of face mask 10. Strap 22 may be elastic and/or adjustable. Extensions 16 may also protrude along the top and/or bottom of face mask 10 as well as on the sides. The size of face mask 10 may vary so long as ample space for breathing is maintained between the wearer's face and the mask. Also, the size of eye area 11 may vary to accommodate various goggle sizes.

Various other changes may be made in the illustrative embodiments of the invention shown and/or described herein without departing from the scope of the invention as defined in the appended claims.

Having fully described my invention, I claim:

1. A shield for protecting a wearer's face from liquids, light solids, particles and objects in the air comprising: a face mask for use with goggles that have eyepiece parts and means for attaching said goggles to said face mask and molded in the abstract shape of said wearer's face having: (a) curved portions covering said face's curved forehead and sides of the face and (b) openings in the eye areas adapted to accommodate the eyepiece parts of said goggles and (c) a portion covering said face's nose, mouth, and chin with a curved portion covering under-the-chin and (d) lateral extensions protruding on each side of said face mask to protect said wearer's ears and neck portions and (e) seal means surrounding said openings in said eye areas and sealingly engageable with said eyepiece parts of said goggles and (f) openings for engaging said goggles' attachment means.

2. A shield as recited in claim 1 in which said face mask is formed of polymeric material.

3. A shield is recited in claim 2 in which ample space is provided between the wearer's face and said face mask for use of breathing equipment.

4. A shield as recited in claim 1 including said goggles, said goggles having curved eyepiece parts; said openings for engaging said goggles' attachment means comprising an opening on each side of said face mask; said goggles' attachment means including a strap having two ends and a lug positioned on each side of said goggles, each lug extending through a different one of said openings in the side of said face mask, one end of said strap being attached to said lug on said goggles extended through said opening on one side of said face mask and the other end of said strap being attached to said lug on said goggles extended through said opening on the other side of said face mask; and a thin locking member engaging said strap on one side of said face mask to lock said strap attachment means to said one side of said face mask and another thin locking member engaging said strap on the other side of said face mask to lock said strap attachment means to said other side of said face mask.

5. A shield as recited in claim 4 in which each lug contains two spaced apart projections, one end of said strap being attached to the projections on one said lugs and the other end of said strap being attached to the projections on the other side of said lugs.

6. A shield as recited in claim 5 in which said face mask is formed of polymeric material.

* * * * *